United States Patent [19]

Dugenet et al.

[11] Patent Number: 4,783,194
[45] Date of Patent: Nov. 8, 1988

[54] PROCESS FOR THE BACTERIAL DECONTAMINATION OF TEXTILES COMPRISING UNCOMPLEXED CALCIUM

[75] Inventors: Yann Dugenet, Houilles; Pierre Isoard, Villeurbanne; Jean-Claude Kerleaux, Trevoux, all of France

[73] Assignee: Atochem, France

[21] Appl. No.: 34,742

[22] Filed: Apr. 6, 1987

[30] Foreign Application Priority Data

Apr. 11, 1986 [FR] France ................... 86 05409

[51] Int. Cl.$^4$ .................... C11D 7/54; D06L 3/02; D06L 3/16
[52] U.S. Cl. ......................... 8/111; 252/106; 252/103; 8/137
[58] Field of Search ............. 252/111, 106, 103; 8/137, 111

[56] References Cited

U.S. PATENT DOCUMENTS 4,319,973 3/1982 Porta .................... 204/133
4,623,357 11/1986 Urban ....................... 8/107

FOREIGN PATENT DOCUMENTS 0047015 9/1987 European Pat. Off. .
0086511 9/1987 European Pat. Off. .
0109279 9/1987 European Pat. Off. .
2532866 9/1987 Fed. Rep. of Germany .
2573452 9/1987 France .

Primary Examiner—John F. Niebling
Assistant Examiner—Isabelle Rodriquez
Attorney, Agent, or Firm—Sigalos, Levine & Montgomery

[57] ABSTRACT

A process for decontaminating textiles contaminated by bacteria comprising washing said textiles with a detergent composition free of any peroxide bleaching agent, and then treating said textiles with a peroxide bleaching agent in an aqueous bath at a pH of between about 9 and 13, at a temperature of between about 40° to 70° C., in the presence of calcium, for a time sufficient to decontaminate said textiles; said calcium rendered soluble and uncomplexed and being present in an amount between about 0.001 to 1% by weight based on the weight of the bath with the source of calcium being selected from calcium oxide, calcium hydroxide, or a calcium salt whose anion is inert with respect to the peroxide bleaching agent and whose dissociation constant is above about 0.01.

9 Claims, No Drawings

PROCESS FOR THE BACTERIAL DECONTAMINATION OF TEXTILES COMPRISING UNCOMPLEXED CALCIUM

BACKGROUND OF THE INVENTION

The present invention relates to a process of decontaminating (disinfecting) textiles contaminated with bacteria.

The presence of certain bacteria on textiles being the cause of serious pathogenic risks, such a decontamination is of obvious interest in the field of hygiene; in particular, in the field of domestic or group hygiene, for instance in the hospital environment.

Although certain bacteria, such as *Pseudomonas aeruginosa* are very sensitive to conventional disinfectants, such as for instance hypochlorite, others are of such virulence that the need to destroy them can justify destruction of the textile itself which they contaminate. In the most general case, however, when, for example, there is a contamination of the textiles by bacteria such as non-spore forming bacteria; e.g. *Streptococcus fecalis, Staphylococcus aureus* (*S. aureus*), or *Escherichia coli* (*E. coli*), treatments are searched for which preserve the initially contaminated textiles.

The economic justification of such treatments must, however, remain compatible with a sufficiently effective bactericidal effect, which no longer is the case when the textiles are subjected to a detergent action at a temperature below about 70° C.

That is what is brought out for instance by the article by Joanne C. Wiksell, Mary S. Pickett and Paul A. Hartmann in Applied Microbiology, 25, No. 3, March 1973, pp. 431–435.

A modification of the detergent treatment then becomes required, which consists of resorting to a chlorinated disinfectant such as, for instance, sodium hypochlorite or chlorinated organic compounds.

That is, for instance, what William G. Walter and John B. Shillinger recommend in Applied Microbiology, 29, No. 3, March 1975, pp. 368–373 or Robert R. Christian, Janet T. Manchester and Michael T. Mellori in Applied and Environmental Microbiology, 45, No. 2, February 1983, pp. 591–597.

Disinfection in the presence of active chlorine, however, presents as major drawbacks the involvement of the risk of corrosion of the treatment istallations, the necessity of a subsequent neutralization and, in the case of hypochlorite; the disinfectant most commonly used, the irreversible appearance in the form of colored stains of chlorohexidene or its derivatives, of the family of bis-diguanides, another class of disinfectants very much used in the hospital environment.

SUMMARY OF THE INVENTION

The process according to the invention does not present the drawbacks of the known processes and results in a high bactericidal effect at a low temperature without the intervention of a chlorinated disinfectant.

Briefly, the present invention comprises a process for decontaminating textiles contaminated by bacteria comprising washing said textiles with a detergent composition free of any peroxide bleaching agent, and then treating said textiles with a peroxide bleaching agent in an aqueous bath at a pH of between about 9 and 13, at a temperature of between about 40° to 70° C., in the presence of calcium, for a time sufficient to decontaminate said textiles; said calcium rendered soluble and uncomplexed and being present in an amount between about 0.001 to 1% by weight based on the weight of the bath with a source of calcium being selected from calcium oxide, calcium hydroxide, or a calcium salt whose anion is inert with respect to the peroxide bleaching agent and whose dissociation constant is above about 0.01.

By the process according to the invention characterized as above, we mean a process in which the detergent washing operation which precedes the action of the peroxide agent is continued or not continued after that action has taken place. In the first case, it is well understood that the detergent washing operation and also the disinfection can be finished very much beyond a reduction of at least $10^5$ times of the number of countable bacteria.

DETAILED DESCRIPTION

In accordance with the present invention, a quantity of calcium rendered soluble and not bound in complexes of at least about 0.001% and not exceeding about 1% is sufficient for the desired result to be ensured with an amount not exceeding about 0.1% most often being sufficient. Calcium chloride is the most common example of salt used as a source of calcium in the invention although calcium oxide, calcium hydroxide, or any other calcium salt whose anion is inert with respect to the peroxide bleaching agent and whose dissociation constant is above 0.01 can be used.

The peroxide bleaching agent present in the bath can be any conventional one used in bleaching, but is preferably selected; for example, from among hydrogen peroxide, sodium perborate, sodium pecarbonate, or urea peroxyhydrate.

The concentration in active oxygen resulting from the presence of such bleaching agents is generally between 0.01% and 0.05% by weight in relation to the weight of the bath.

The bath can contain complexing agents of metallic ions; in particular alkaline earth metal ions, in such a quantity that the amount of calcium rendered soluble and not bound in complexes as set forth above is adhered to.

The bath can finally be constituted only of the aqueous mixture of the alkaline agent, of the peroxide bleaching agent, and of the salt selected to be the source of calcium. In such case, the bath preferably contains the calcium and the alkaline agent in the ratio which would correspond to the formation of $Ca(OH)_2$.

The preferred alkaline agent is sodium hydroxide (NaOH), but the product which is the source of calcium can be the source, in totality or in part, of the alkalinity of the bath when it is selected from among calcium oxide or calcium hydroxide.

The preferred pH range is from 10.5 to 12.5.

The treatment duration largely depends on the degree of contamination and other conditions adopted to carry out this operation. It is generally less than, for instance, 30 minutes and most often less than 15 minutes.

As far as the detergency operation is concerned, it is carried out in any known manner, advantageously indeed at a temperature below 70° C., most generally between 30° C. and 70° C., in an alkaline bath, in the presence; in type and in quantity, of detergent products and of other ingredients usually employed; like alkylbenzenesulfonates and alkylarylbenzenesulfonates, ethoxylated fatty alcohols, sodium tripolyphosphate or its substitution products, antiredeposition agents like carboxymethylcellulose, mineral salts like sodium silicate or magnesium silicate, sodium sulfate, complexing agents, bluing products, perfumes, and the like in their usual amounts.

The process of the invention is applicable to textiles made of natural fibers, like cotton, or textiles based on synthetic fibers, like polyester cotton, which may or may not require to be bleached and/or washed.

The invention will be further described in connection with the following examples which are set forth for purposes of illustration only.

In these examples, two different textiles, representative of those used in current practice, namely 100% cotton and 65% polyester-35% cotton, in the form of cloths have served for the preparation of circular samples of 50 mm diameter which each were contaminated experimentally by deposition at their center of 500 microliters of a bacterial suspension of *E. coli,* reference strain 54127 of the National Collection of Microorganism Cultures (CNCM) of the Pasteur Institute in Paris, corresponding to reference 10536 of the American Type Culture Collection (ATCC), or else of a bacterial suspension of *S. aureus,* reference strain Oxford CNMC 53154 corresponding to reference ATCC 9144.

The inoculum serving for the contamination originates from a culture in liquid medium of the test organism for 18 hours at 30° C.

The bacterial suspensions are counted by spreading out on nutritive agar according to the process described in French standard AFNOR NF T 72-190, March 1981.

The values of the bacterial count in this case, as in all that follows, are converted into decimal logarithms and are expressed in that form.

The samples corresponding to the tests with *E. coli* are designated by the letter "E" in the description which follows and those corresponding to the tests with *S. aureus* by the letter "S".

After contamination, E and S are grown for 1 hour to 37° C. in a ventilated drying oven prior to being sterilely incorporated by pinning, each on their side, to a charge of white cloth of 15 kg and to being subjected with this charge, respectively and separately, to the decontamination process of the invention or to a process carried out for the sake of comparison.

The disinfection terminated, E and S are the object of a sterile sampling in the charge and are treated in order to extract the still live bacteria, if necessary, and to proceed with the bacterial count of the corresponding extraction liquids E and S, according to a process analogous to the one described in the French AFNOR standard already cited.

The samples $E_e$ and $S_e$ resulting from the extraction treatment of bacteria are themselves subjected to a bacterial count by proceeding as for the filtering membranes in the French AFNOR standard already cited, by analysis of the colonies which have appeared, if the occasion arises, after 48 hours of incubation at 30° C.

EXAMPLES 1 TO 12

These examples illustrate the invention when the treatment associated with the detergency operation is carried out intermediately between two detergent treatments.

The equipment used is a DUBIX A2 S15 ® type washer-dryer.

After wetting of the charge of 15 kg of cloth including the contaminated sample E or S, the first detergent treatment is carried out at 40° C. for 4 minutes by means of a washing composition free of peroxide bleaching agent, ORIX MAJOR - Saint Marc ® brand, used at a rate of 10 g/kg dry cloth, the weight ratio of bath/dry cloth charge being 3/1.

After drying for 1 minute, an operation moreover optional provided that the pH conditions are adhered to in the associated treatment, the latter is carried out with a weight ratio of bath/dry cloth (linen) charge of 5/1, at 60° C. for 9 minutes, in the presence of 39.5 g of hydrogen peroxide, of 1.5 g of calcium not bound in complexes introduced in the form of chloride dihydrate $CaCl_2 \times 2H_2O$, and of 3 g of sodium hydroxide introduced in the form of a commercial solution.

A second detergent wash treatment is carried out directly after the above treatment, at 60° C. for 6 minutes under the conditions of bath ratio, of type and of quantity of washing product identical to the ones cited for the first detergent treatment.

After rinsing and ordinary final drying, the bacterial counts of samples E or S are made as described above.

The results of disinfection are set forth in Table I below.

TABLE I

| Treatment associated with the detergency operation carried out between two detergent treatments. | | | | | | | | | |
|---|---|---|---|---|---|---|---|---|---|
| | E | | | | S | | | | |
| | Number of Bacteria (1) | | | | Number of Bacteria (1) | | | | |
| | | After | | | | | After | | |
| | | Cotton | | Polyester-Cotton | | | Cotton | | Polyester-Cotton |
| Example No. | Before | $E_1$ | $E_e$ | $E_1$ | $E_e$ | Before | $S_1$ | $S_e$ | $S_1$ | $S_e$ |
| 1 | 8.0 | 0 | 0 | | | | | | | |
| 2 | 8.9 | 0 | 0 | | | | | | | |
| 3 | 8.5 | 0 | 0 | | | | | | | |
| 4 | 8 | | | 0 | 0 | | | | | |
| 5 | 8.9 | | | 0 | 0 | | | | | |
| 6 | 8.5 | | | 0 | 0 | | | | | |
| 7 | | | | | | 7.4 | 0 | 0 | | |
| 8 | | | | | | 8.5 | 0 | 0 | | |
| 9 | | | | | | 8.4 | 0 | 0 | | |
| 10 | | | | | | 7.4 | | | 0 | 0 |
| 11 | | | | | | 8.5 | | | 0 | 0 |
| 12 | | | | | | 8.4 | | | 0 | 0 |

(1) Bacterial counts expressed, as cited above, by their decimal logarithms.

EXAMPLE 13

Example 13 illustrates a process given by way of comparison, which uses a chlorinated disinfectant, sodium hypochlorite.

In the same machine as for the preceding examples and after wetting, the cloth charge is subjected to two successive detergent treatments carried out with a weight ratio of bath/dry cloth charge equal to 3, the first one for 4 minutes at 40° C. in the presence of 10 g/kg of dry cloth of the washing composition used in the other examples, the second one for 6 minutes at 60° C. in the presence of that same washing composition used again at a rate of 10 g/kg of dry cloth.

After rinsing, a treatment with a weight ratio of bath/dry cloth charge equal to 5 takes place for 7 minutes at 30° C. in the presence of sodium hypochlorite used at a rate of 10 cm³ of sodium hypochlorite solution of 48 chlorometric degrees per kilogram of dry cloth and is followed by a neutralization of the medium by sodium bisulfite prior to rinsing and final drying.

With the samples of cotton or of polyester cotton of type E (*E. coli*), the degree of disinfection attained is then uncertain, the disinfection can sometimes be complete, and sometimes clearly insufficient compared to the systematic absence of microorganisms observed in all of the cases of operating according to the process of the invention.

An average of three tests leads, for instance, to a count close to 1 in the case of cotton and to 0.5 in the case of polyester-cotton starting from a count of 8.6.

With cotton samples of type S (*S. aureus*) the degree of disinfection is even lower as shown by Table II below.

TABLE II

| Cotton Samples of Type S | | |
|---|---|---|
| Number of Bacteria | | |
| Before | After | |
| | $S_1$ | $S_e$ |
| 8.3 | 0 | 4 |
| 8.1 | 2.6 | 4.8 |
| 8.1 | 4.3 | 3.8 |

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A process for decontaminating textiles contaminated by bacteria comprising washing said textiles with a detergent composition free of any peroxide bleaching agent, and then treating said textiles with a peroxide bleaching agent in an aqueous bath at a pH of between about 9 and 13, at a temperature of between about 40° to 70° C., in the presence of calcium, for a time sufficient to decontaminate said textiles; said calcium rendered soluble and uncomplexed and being present in an amount between about 0.001 to 1% by weight based on the weight of the bath with the source of calcium being selected from calcium oxide, calcium hydroxide, or a calcium salt whose anion is inert with respect to the peroxide bleaching agent and whose dissociation constant is above about 0.01.

2. The process of claim 1 wherein by the quantity of calcium rendered soluble and not bound in complexes is less than 0.1%.

3. The process of claim 2 wherein the source of calcium is calcium chloride.

4. The process of claim 3 wherein the peroxide bleaching agent is selected from hydrogen peroxide, sodium perborate, sodium percarbonate, or urea peroxyhydrate.

5. The process of claim 4 wherein the quantity of peroxide bleaching agent corresponds to a concentration in active oxygen of between about 0.01% and 0.05% by weight based on the weight of the bath.

6. The process of claim 5 wherein the bath in which the peroxide bleaching agent acts contains complexing agents of alkaline earth metals.

7. The process of claim 6 wherein the bath in which the peroxide bleaching agent acts has a pH between about 10.5 and 12.5.

8. The process of claim 7 wherein the action of the peroxide bleaching agent is exerted on the contaminated textiles for a time not exceeding 15 minutes at the selected temperature.

9. The process of any one of claims 1 to 8 wherein the detergent washing is carried out at a temperature between at least equal to 30° C. and at the most equal to 70° C.

* * * * *